US012485235B2

(12) United States Patent
Sivarasu et al.

(10) Patent No.: US 12,485,235 B2
(45) Date of Patent: Dec. 2, 2025

(54) ASSISTIVE DEVICE FOR AN INHALER

(71) Applicant: University of Cape Town, Cape Town (ZA)

(72) Inventors: Sudesh Sivarasu, Cape Town (ZA); Giancarlo Lanfranci Beukes, Cape Town (ZA); Jason Dirk Voorneveld, Cape Town (ZA); Michael Levin, Cape Town (ZA); Yasheen Brijlal, Cape Town (ZA); Gokul Arjunan Nair, Cape Town (ZA); George Alexis Hugo, Cape Town (ZA)

(73) Assignee: University of Cape Town, Cape Town (ZA)

( * ) Notice: Subject to any disclaimer, the term of this patent is extended or adjusted under 35 U.S.C. 154(b) by 1001 days.

(21) Appl. No.: 17/542,753

(22) Filed: Dec. 6, 2021

(65) Prior Publication Data

US 2022/0088325 A1 Mar. 24, 2022

Related U.S. Application Data

(63) Continuation-in-part of application No. 16/087,362, filed as application No. PCT/IB2017/051462 on Mar. 14, 2017, now Pat. No. 11,213,636.

(30) Foreign Application Priority Data

Mar. 21, 2016 (GB) ..................................... 1604709

(51) Int. Cl.
*A61M 15/00* (2006.01)

(52) U.S. Cl.
CPC ...... *A61M 15/009* (2013.01); *A61M 15/0021* (2014.02); *A61M 2205/586* (2013.01); *A61M 2205/59* (2013.01)

(58) Field of Classification Search
CPC .. A61M 15/009; A61M 15/0021–0026; A61M 2205/586; A61M 2205/59; A61M 15/0075
See application file for complete search history.

(56) References Cited

U.S. PATENT DOCUMENTS 5,899,365 A 5/1999 Eichler et al.
11,213,636 B2 1/2022 Sivarasu et al.
(Continued)

FOREIGN PATENT DOCUMENTS

EP 1066075 A1 1/2001
WO WO-96/11152 A1 4/1996
(Continued)

OTHER PUBLICATIONS

Combined Search and Examination Report under Sections 17 and 18(3) for Application No. GB1604709.4, dated Aug. 18, 2016 (5 pages).
(Continued)

*Primary Examiner* — Elliot S Ruddie
(74) *Attorney, Agent, or Firm* — Clark & Elbing LLP

(57) ABSTRACT

An assistive device for a metered dose inhaler decreases the force required to operate the inhaler. The assistive device has a body with a passage for receiving a replaceable conventional metered dose inhaler assembly that has a canister and a transverse mouthpiece with an axis of the canister aligning approximately with that of the passage. At least two symmetrically arranged levers extend in a direction away from the body and parallel to an axis thereof. A proximal end of each lever is attached to the body such that the free opposite ends of the levers may be moved towards and away from each other. An inwardly directed cam surface on each of the lever exerts a force on an end of the canister in use to move
(Continued)

the canister longitudinally to cause a dose of medicament to be dispensed from the canister. An optional dose counter may form part of the device.

19 Claims, 14 Drawing Sheets

(56) References Cited

U.S. PATENT DOCUMENTS

| | | | | |
|---|---|---|---|---|
| 2001/0013343 | A1 | 8/2001 | Andersson | |
| 2003/0084899 | A1 | 5/2003 | Andersson | |
| 2004/0245291 | A1 | 12/2004 | Simon et al. | |
| 2005/0194006 | A1 | 9/2005 | Hoang | |
| 2006/0191959 | A1* | 8/2006 | Davies | B05B 11/1056 222/402.15 |
| 2008/0168984 | A1 | 7/2008 | Lintern et al. | |
| 2008/0190419 | A1 | 8/2008 | Pearson et al. | |
| 2009/0229604 | A1 | 9/2009 | Pearson et al. | |
| 2010/0078490 | A1* | 4/2010 | Fenlon | A61M 15/009 116/284 |
| 2013/0139814 | A1 | 6/2013 | Mullane et al. | |
| 2014/0318534 | A1 | 10/2014 | Engelbreth | |
| 2016/0129206 | A1 | 5/2016 | Engelbreth | |

FOREIGN PATENT DOCUMENTS

| | | | |
|---|---|---|---|
| WO | WO-2006/097728 | A1 | 9/2006 |
| WO | WO-2006/097745 | A1 | 9/2006 |
| WO | WO-2006/097756 | A1 | 9/2006 |
| WO | WO-2007/028992 | A1 | 3/2007 |
| WO | WO-2008/110584 | A2 | 9/2008 |
| WO | WO-2014/140724 | A1 | 9/2014 |

OTHER PUBLICATIONS

International Search Report for International Patent Application No. PCT/IB2017/051462, mailed Sep. 20, 2017 (6 pages).

Written Opinion of the International Searching Authority for International Patent Application No. PCT/IB2017/051462, mailed Sep. 20, 2017 (8 pages).

* cited by examiner

ASSISTIVE DEVICE FOR AN INHALER

CROSS-REFERENCE(S) TO RELATED APPLICATIONS

This application is a continuation in part of U.S. patent application Ser. No. 16/087,362 filed 21 Sep. 2018, which is the United States National Phase of International PCT Application No. PCT/IB2017/051462 filed 14 Mar. 2017, which claims priority from United Kingdom Patent Application No. 1604709.4 filed on 21 Mar. 2016, the disclosures of which are hereby incorporated by reference herein.

FIELD OF THE INVENTION

This invention relates to an assistive device for an inhaler whereby medication can be administered to a patient for delivering medication to the body via the respiratory system and, more particularly, to an assistive device that can be configured to effectively reduce the force necessary to administer medication from an inhaler. Such an assistive device it is envisaged would be particularly useful to paediatric and geriatric patients that may have difficulty in applying sufficient force to an inhaler to release the medication.

In particular, but not exclusively, the invention relates to an assistive device for metered dose inhalers that is a rather common form of inhaler currently available.

BACKGROUND TO THE INVENTION

An inhaler is a handheld aerosol device that uses a propellant to deliver a therapeutic agent. An inhaler typically includes a pressurized metal canister that contains the pharmacological agent in suspension or solution, a surfactant, and a propellant with the metal canister being fitted with a discharge valve that in the case of a metered dose inhaler takes the form of a metering valve. The canister is generally housed in a plastic sleeve that has a mouthpiece for drug delivery. Actuation or triggering of the canister produces a fine atomized spray that delivers a dose. In the case of a metered dose inhaler the delivery typically takes place over a time period of about 100-200 milliseconds which varies according to the particular medication and application.

To actuate the conventional manually operable inhaler, the user applies an axially directed compressive force to the closed end of the canister. The internal components of the discharge of metering valve assembly are spring loaded so that a compressive force reportedly of about 15 to 30 N, and sometimes more, is required to activate the device. In response to this compressive force, the canister moves axially with respect to the valve stem by an amount varying from about 2 to about 4 mm which is sufficient to actuate the discharge or metering valve and cause a quantity of the drug and propellant to be expelled through a valve stem. A user inhaling through the drug delivery outlet of the inhaler device at this point thereby receives a dose of the drug.

The force needed to administer a dose is considerable to some patients of lesser physical ability, in particular children and geriatrics. Such persons are sometimes unable to exert the required force or at least have considerable difficulty in doing so. In order to combat this, more sophisticated inhaler devices have been proposed and are available commercially, but these are not affordable to many of lesser means. Some sophisticated devices even use the patient's breath to activate them but they are considerably more costly than a simple inhaler device.

For example, United States publication US2003084899 describes an inhalation device in which diametrically opposite actuating members are hingedly attached to sidewalls of a body member with the point of physical application of force to the actuating members being between the hinged attachment to the sidewalls of the body and inclined inwardly facing surfaces that engage diametrically opposite bottom corners of an inverted canister and cause the dispensing of a dose of medicament. The result is a third order lever system in which the resistance (or load) is on one side of the point at which physical effort is applied to the actuating members and the fulcrum is located on the other side of the point of application of the physical effort. The mechanical advantage of such a third order lever system is always less than 1 and it therefore does not assist the user from a physical perspective. Also, with this physical arrangement the range of movement of the actuating members is limited by the presence of the canister in between them. Accordingly, a desired mechanical advantage cannot be achieved in any way with this arrangement.

There is a need for an assistive device that can be used in combination with a conventional inhaler in order to decrease the force required to activate the inhaler.

Conventional metered dose inhalers containing multiple doses typically contain in the range of 100 to 300 and quite commonly about 200 doses. As the canisters are not transparent, a record needs to be made of how many doses have been taken and therefore how many doses remain in the canister. Considerable inventive activity has been exerted towards the creation of effective dose counters some of which are electronic in nature and others of which are purely mechanical. The latter may operate on the basis of a pawl that is movable longitudinally and rotates a toothed wheel one tooth at a time as part of a dose tracking technology. Unfortunately, most of these dose counters are also costly and are not affordable by those of lesser means.

There is therefore also a need for an assistive device that embodies a simple and inexpensive dose counter.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided an assistive device for an inhaler, wherein the assistive device comprises:

- a body defining a passage configured to receive a conventional inhaler assembly, the conventional inhaler assembly including a canister and transverse mouthpiece with an axis of the canister of the inhaler assembly approximately aligning with an axis of the passage through the body of the assistive device,
- a base support associated with the body for supporting the mouthpiece of the inhaler assembly at one end of the body when such an inhaler assembly is installed therein, and
- at least two symmetrically arranged levers supported by the body adjacent the passage and extending in a direction away from the base support and generally parallel to an axis of the body with a proximal end of each of the levers being attached to the body by an attachment that enables a free opposite end of at least one of the levers to be moved towards and away from the other of the levers, and an inwardly directed cam surface of at least one of the levers that is configured to exert a force on a closed end of the canister of the conventional inhaler assembly when it is installed in the assistive device to move the canister longitudinally towards the base support and cause medicament to be dispensed from the canister.

The assistive device may include a height adjuster member disposed between the inwardly directed cam surface and the closed end of the canister. The height adjuster member may be configured to attach to the closed end of the canister to adjust the height of the canister.

There may be two levers symmetrically arranged relative to the passage with the cam surfaces thereof projecting into the passage so as to cooperate with corners of a closed end of the canister or corners of the height adjuster member. The cam surfaces may be curved inwardly and configured to achieve a suitable longitudinal movement of the canister during movement of the levers towards each other so that medication is delivered by appropriate operation of the levers. The cam surfaces may alternatively be curved outwardly to achieve a suitable longitudinal movement of the canister.

The attachment of the at least two symmetrically arranged levers may be a hinge joint configured to return the lever to a starting position in cooperation with a return of the canister to a rest position after dispensing the medicament. The attachment may enable the free opposite ends of two opposing levers to be moved towards each other to move the inwardly directed cam surfaces of the levers.

The base support may include a front outlet configured to support the transverse mouthpiece of the canister.

The assistive device may include a dose counter mechanism in the form of a gear arrangement activated by movement of one of the levers. The gear arrangement may be configured to be activated by at least a partial movement of the lever. The gear arrangement may include a first gear configured to be incremented by a pawl interfacing with the lever and a second gear configured to rotate one increment when the first gear has completed a full revolution, wherein the second gear provides a dial display to display a number of delivered doses.

The at least two symmetrically arranged levers may be in an arrangement complying with a second order lever system in which the mechanical advantage is greater than 1. Lengths of the levers may be selected according to the mechanical advantage to be achieved.

The at least two symmetrically arranged levers may be attached to an end of the body opposite to the end of the body having the base support and extend in a direction away from the body.

In accordance with another aspect of the invention there is provided an assistive device for an inhaler, wherein the assistive device comprises:

a body configured to removably receive the inhaler substantially within the body, the body including a base support configured to engage with a mouthpiece end of the inhaler;

two opposed levers extending longitudinally from the body at an opposite end of the body to the base support, wherein at least one of the levers has a hinge attachment to the body for operation by squeezing the levers together and the at least one of the levers has an inwardly directed cam surface configured to exert a force that is transferred to an operational end of the inhaler as the levers are squeezed together.

The two opposed levers may both have the hinge attachment to the body and the inwardly directed cam surface, with the cam surfaces of the two opposed levers exerting a force in a direction towards the base support of the body.

The inwardly directed cam surface may exert the force on the operational end of the inhaler via an optional height adjustment member. The inwardly directed cam surface may be a curved surface. The inwardly direction cam surface may be a convex curved surface or a concave curved surface.

The base support may be configured to engage with the mouthpiece of the inhaler.

The assistive device may include a dose counter mechanism in the form of a gear arrangement activated by movement of one of the levers, wherein the gear arrangement is configured to be activated by at least a partial movement of the lever.

In accordance with another aspect of the invention there is provided an assistive device for an inhaler wherein the assistive device comprises a body defining a passage configured to receive a conventional inhaler assembly including a canister and transverse mouthpiece with an axis of the canister of the inhaler assembly approximately aligning with an axis of the passage through the body of the assistive device, a foot associated with the body for supporting a mouthpiece of the inhaler assembly at one end of the body when such an inhaler assembly is installed therein, and at least two symmetrically arranged levers supported by the body adjacent the passage and extending in a direction away from the foot and generally parallel to an axis of the body with a proximal end of each of the levers being attached to the body by an attachment that enables free opposite ends of the levers to be moved towards and away from each other, and an inwardly directed cam surface on each of the levers that is configured to engage a closed end of a canister of a conventional inhaler assembly when it is installed in the assistive device to move the canister longitudinally towards the foot and cause medicament to be dispensed from the canister.

Further features of the invention provide for the foot to be carried by a leg extending from the body; for the length of the leg to be telescopically adjustable to accommodate different lengths of conventional inhaler assemblies; for the leg to have a series of formations along a part of its length that may be selectively engaged by a releasable locking member that in its operative position is axially stationary relative to the body in order to set an adjustable position of the foot relative to the body; for there to be either two or three levers symmetrically arranged relative to the passage with the cam surfaces thereof projecting into the line of the passage so as to cooperate with corners of a closed end of a canister of a conventional inhaler when it is installed in the assistive device with its closed end located on the outside of the body on the side thereof opposite the foot; for the cam surfaces to be curved inwardly and to be designed to achieve a suitable longitudinal movement of a canister during movement of the levers towards each other so that a dose of medication can be delivered by operation of the levers; and for the cross-sectional size of the passage through the body to be adjustable to accommodate different diameters of inhalers; and for the conventional inhaler to be a metered dose inhaler.

Further features of the invention provide for the assistive device to be especially configured for use with a metered dose inhaler and the body of the assistive device has a support on one side thereof that supports a toothed gear dose counting mechanism having the axes of the gears extending at generally right angles to the axis of the passage with one of the toothed gears co-operating with a pawl carried on one end of a transverse arm that has its other end pivotally attached to one of the levers so that it moves transversely relative to the axis of the passage in a reciprocal manner as the levers are moved towards and away from each other; for the pawl driven gear to have radially shorter teeth interposed between radially longer teeth such that only the longer teeth transfer any movement to gears driven by the driven gear; and for the toothed gear mechanism to include a pawl driven gear, a transfer gear, and a display gear carrying numerals that are visible through a suitable aperture to indicate doses remaining or doses already delivered.

It will be understood that the levers in the case of the assistive device according to this invention are in an arrangement complying with that of a second order lever system in which the mechanical advantage is always greater than 1. Furthermore, as the canister is not indeed present between the levers themselves and only between the cam surfaces, the range of movement of the levers towards each other is not restricted by an interposed canister and the design may be such that the levers can move towards each other until they are almost in contact. An appropriate mechanical advantage greater than 1 can therefore be achieved and the design of the levers and cam surfaces can be targeted at achieving a desired mechanical advantage greater than 1.

Whilst both of the two levers or three levers envisaged above may be movable about their proximal ends, it is to be understood that the principles of the invention would also be fulfilled if one lever were fixed relative to the body and, in the case of a two lever arrangement, only the other one would be movable thereby nevertheless rendering the levers movable towards and away from each other.

For paediatric purposes the assistive device could be made to resemble a comic character in which instance the aperture could be a mouth or eye through which the number of remaining or delivered doses can be viewed and an outer cover for the gear mechanism could support a comic face for example. It would be preferred that only two levers be used in such an instance and they could be made to resemble long ears, for example, such as of a rabbit.

In order that the invention may be more fully understood, one embodiment thereof will now be described by way of example only with reference to the accompanying drawings.

DETAILED DESCRIPTION WITH REFERENCE TO THE DRAWINGS

An assistive device for an inhaler is provided as exemplified in the following embodiments. The assistive device has a body configured to removably receive the inhaler such that it is held substantially within the body. The body includes a base support configured to engage with a mouthpiece end of the inhaler to provide a brace against which the operation of the assistive device is carried out. The assistive device includes two opposed levers extending longitudinally from the body at an opposite end of the body to the base support. At least one of the levers has a hinge attachment to the body for operation by squeezing the levers together and has an inwardly directed cam surface configured to exert a force on an operational end of the inhaler as the levers are squeezed together. In the described embodiments, both levers have the hinge attachment to the body and the inwardly directed cam surface, with the cam surfaces of the two opposed levers exerting a force in a direction towards the base support of the body. The cam surfaces may be flat plates or may be convexly curved to transfer a higher force component in the longitudinal direction of the body.

Figure 1:
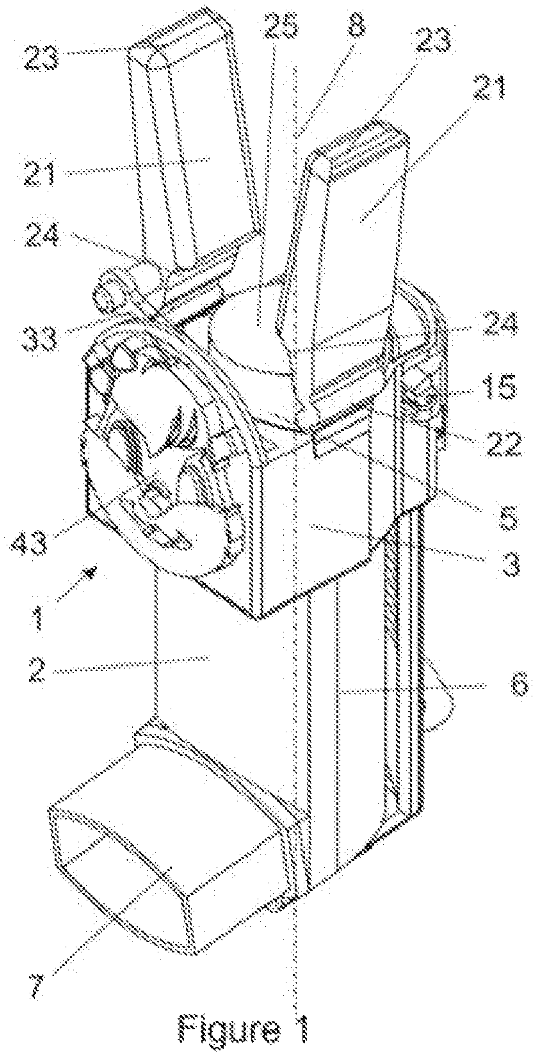
FIG. 1 is a perspective view of a first embodiment of an assistive device according to the invention showing a conventional metered dose inhaler in position in the device.
Figure 2:
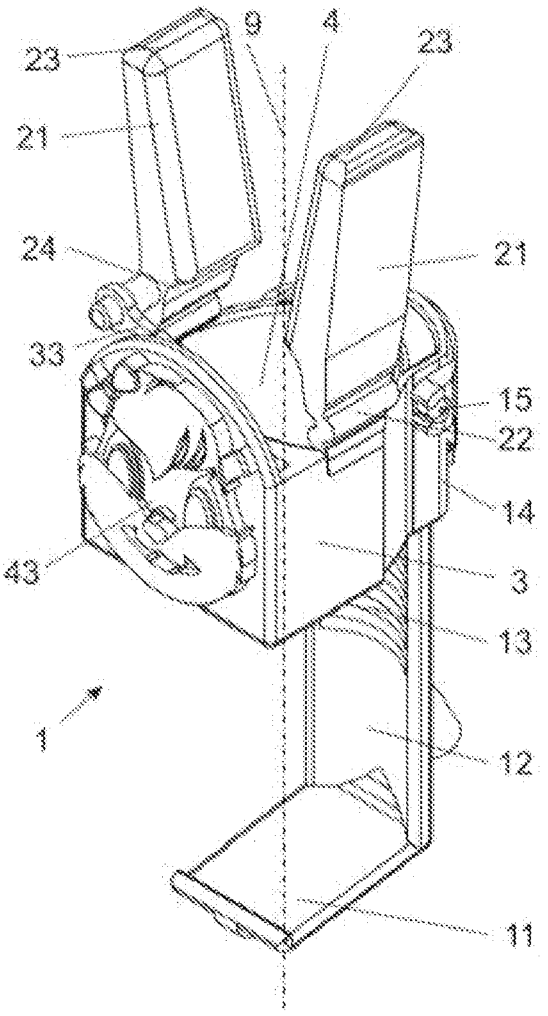
FIG. 2 is a similar view of the embodiment of FIG. 1 with the metered dose inhaler removed.
Figure 7:
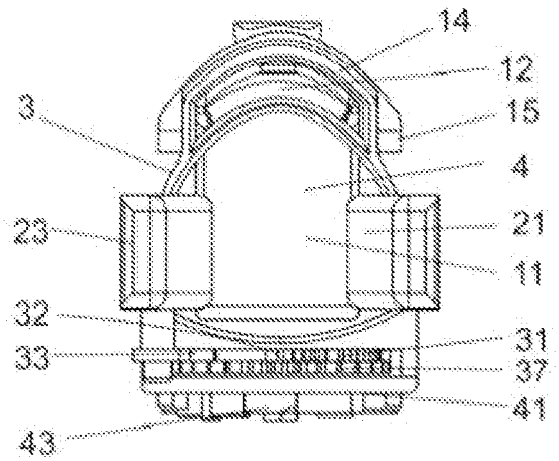
FIG. 7 is a plan view of the assistive device of FIG. 1 with the metered dose inhaler removed.
Figure 5:
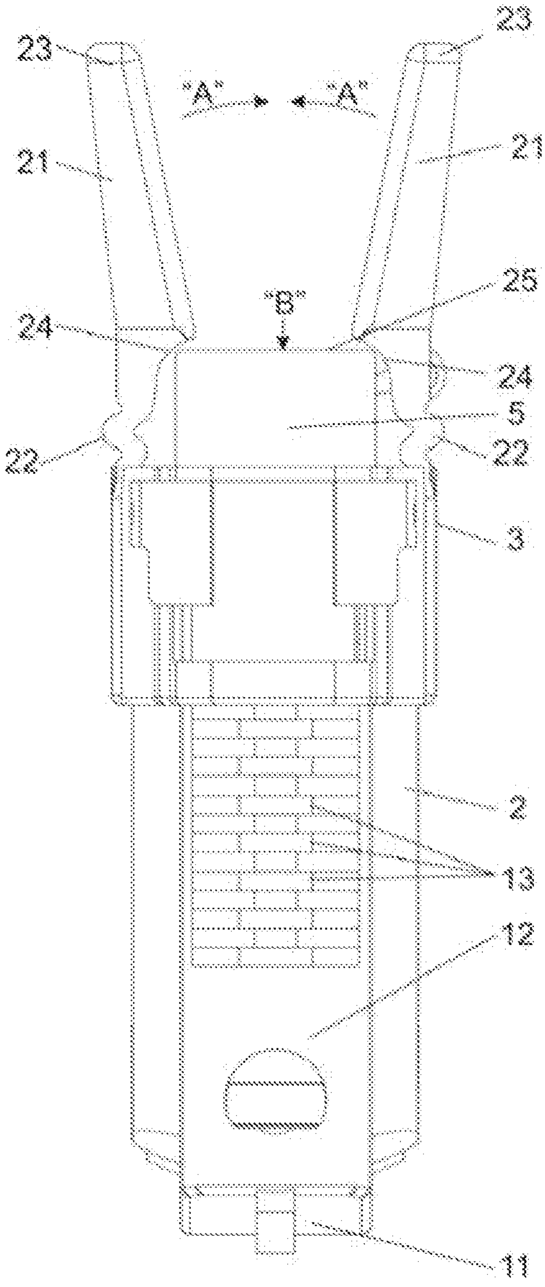
FIG. 5 is a somewhat enlarged rear view of the assistive device of FIG. 1 with the metered dose inhaler in place and showing the relationship between the end of the inhaler canister and the levers.
Figure 6:
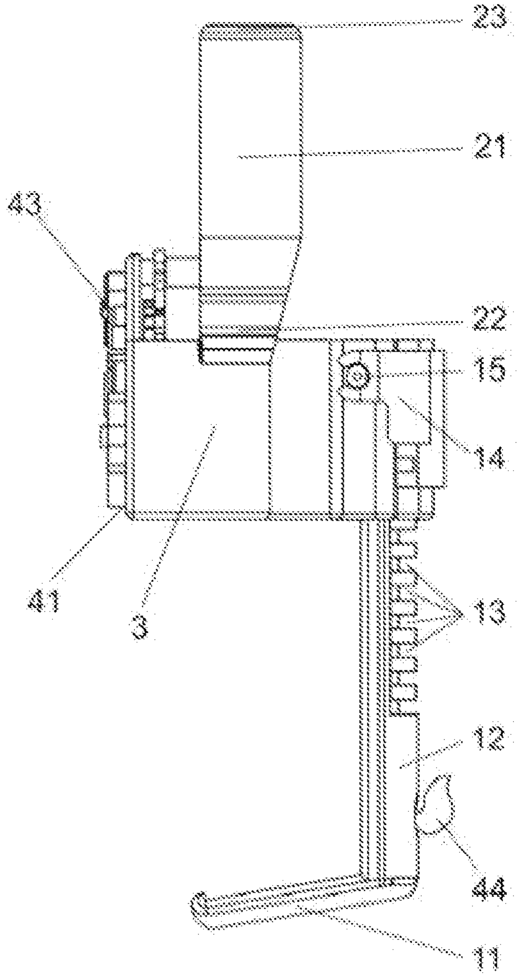
FIG. 6 is a side view of the assistive device of FIG. 1 with the metered dose inhaler removed.

Referring to FIGS. 1 to 8, a first embodiment of an assistive device is illustrated. In the first embodiment, an assistive device, generally indicated by numeral (1), for a metered dose inhaler (2) comprises a body (3) defining a passage (4) configured to receive a conventional metered dose inhaler assembly. The metered dose inhaler includes a canister (5) fitted with the usual outer sleeve (6) having a transverse mouthpiece (7) with an axis (8) of the canister of the inhaler assembly approximately aligning with an axis (9) of the passage through the body of the assistive device. The inhaler assembly is illustrated in FIGS. 1 and 5. The cross-sectional shape of the passage conforms to the cross-sectional shape of the inhaler that is typically basically a somewhat rounded D-shape.

A foot (11) supports the mouthpiece of the metered dose inhaler assembly at one end of the body when such a metered dose inhaler assembly is installed therein. The foot is carried by a leg (12) extending from the body with the length of the leg being telescopically adjustable relative to the body to accommodate different lengths of conventional metered dose inhaler assemblies. The leg has a series of formations in the form of transverse grooves (13) along a part of its length that may be selectively engaged by a releasable locking member (14) that in its operative position is axially stationary relative to the body. The locking member is rotatable between inoperative and operative positions about pivots (15) formed integral with the body and it has projections corresponding to the grooves with two projections conveniently being engaged with the leg by way of a window through the wall of the body.

Two symmetrically arranged levers (21) are supported by the body adjacent the passage and the levers extend in a direction away from the foot and generally parallel to the axis (9) of the body with a proximal end (22) of each of the levers being attached to the body by an attachment that is optionally integral to create living hinges and is configured to enable free opposite ends (23) of the levers to be moved towards and away from each other in a generally arcuate manner. Of course, the levers may be attached to the body by means of pivots or hinges but that would quite possibly increase the cost of the assistive device somewhat which may or may not be significant.

Each lever has an inwardly directed curved cam surface (24) that is configured to engage a closed end (25) of a canister of a conventional metered dose inhaler assembly when it is installed in the assistive device to move the canister longitudinally towards the foot and cause a dose of medicament to be dispensed from the canister. The relationship between the canister end and the cams on the levers is shown clearly in FIG. 5.

The cam surfaces project partially into the line of the passage so as to be in line with diametrically opposite corners of a circular closed end of a canister of a conventional metered dose inhaler when it is installed in the assistive device with its closed end projecting from the side of the body opposite the foot. The cam surfaces are curved inwardly and are designed to achieve a suitable longitudinal movement of a canister during movement of the levers towards each other to deliver a dose of medicament.

As indicated in FIG. 5, inward arcuate movement of the levers as indicated by arrows “A” is translated by the cam surfaces in to longitudinal movement as indicated by arrow “B” of the canister towards the foot to cause a dose of medicament to be dispensed from the canister. The shape of the cam surfaces can accordingly be varied as may be appropriate or desired so that it achieves these basic objectives when the levers are moved towards each other about their attachments to the body.

The lengths of the levers can be selected according to the mechanical advantage to be achieved coupled with the limitation that the levers should not be too long as that may restrict their arcuate movement and also make them rather cumbersome. However, a certain minimum length would be required in order to achieve the objectives of the invention.

The levers may be resiliently biased to their outer positions independently of the canister or they may be urged to their outer positions by spring loading contained within the metering valve assembly of the metered dose inhaler assembly, or both.

The levers are, as indicated above, in an arrangement that complies with the requirements of a second order lever system in which the mechanical advantage is always greater than 1. As the canister is not present between the levers themselves and only between the cam surfaces, the range of movement of the levers towards each other is not restricted by any interposed canister.

Figure 8:
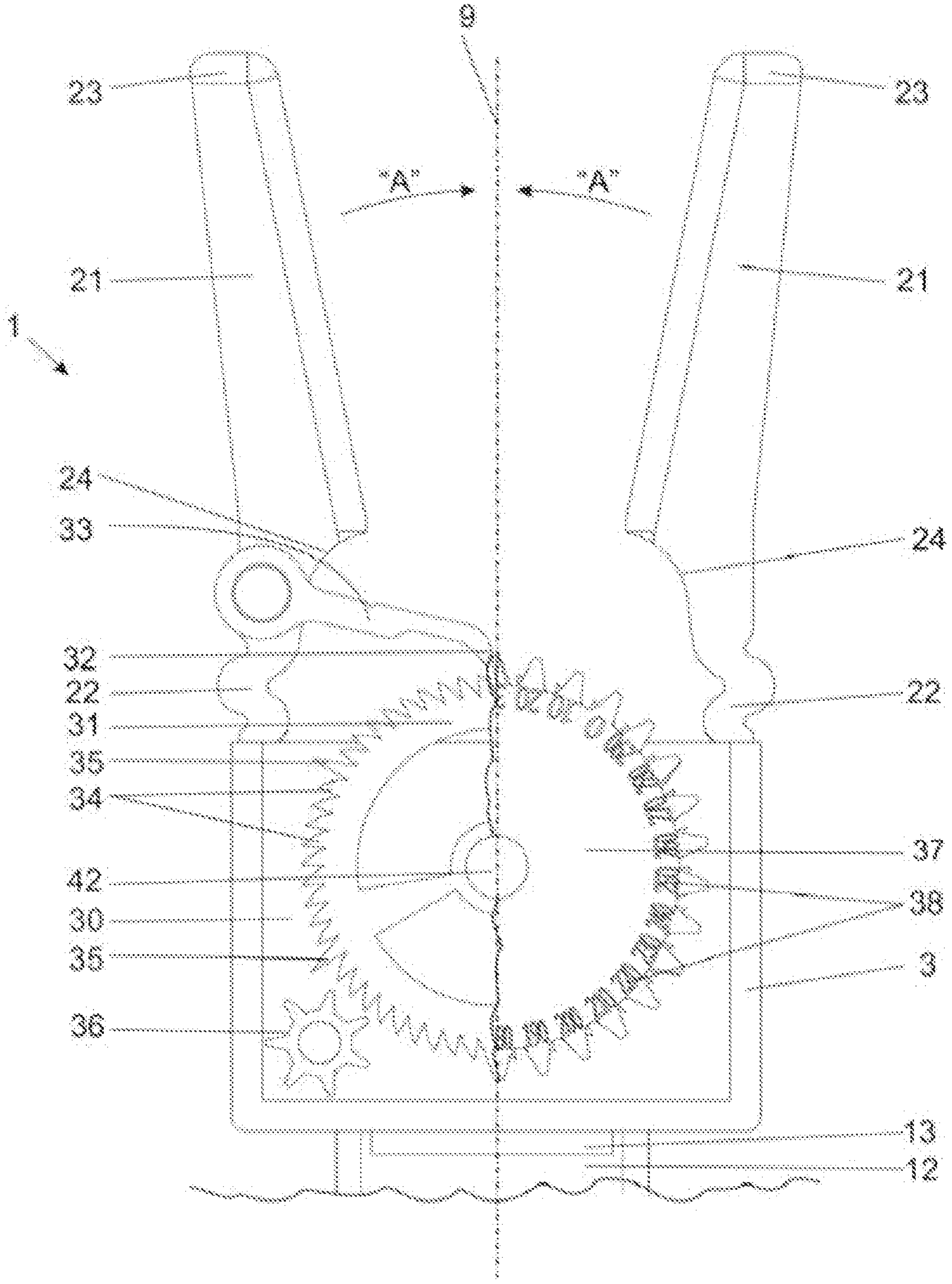
FIG. 8 is an enlarged front view of the body of the assistive device of FIG. 1 with the front removed and the forward display gear partially broken away to reveal the rear pawl driven gear behind it.

As shown most clearly in FIG. 8, the body has a support in the form of a flat face (30) on one side thereof that supports a toothed gear mechanism having the axes of the gears extending at generally right angles to the direction of the axis of the passage. One of the toothed gears is a pawl driven gear (31) that co-operates with a pawl (32) at one end of a transverse arm (33) pivotally attached at its other end to one of the levers (21) so that it moves transversely relative to the axis of the passage in a reciprocal manner as the levers are moved towards and away from each other. This pawl driven gear has radially shorter teeth (34) interposed between radially longer teeth (35) that constitute, in this particular instance, every tenth gear tooth such that only the longer teeth transfer any movement to a transfer gear (36) that cooperates with both the pawl driven gear and with a display gear (37) mounted coaxially with the pawl driven gear.

The display gear (37) carries numerals (38) that are visible through a suitable aperture (39) (see FIG. 3) in a visible front face (41) of the body to indicate doses remaining or doses already delivered. The display gear is rotatable independently about the same axle (42) as the pawl driven gear so that differential angular movements of these two gears are enabled. The arrangement is such that with a total of say sixty teeth on the pawl driven gear (one in ten being of the longer type and the sixty being selected to ensure that the spacing between the teeth results in the required movement of the arm and pawl to effectively result in the rotation of the pawl driven gear) and thirty teeth on the display gear, one revolution of the display gear will correspond to a total of 300 doses if each tooth is provided with a total number in increments of 10 (often 290 if the first one is labelled “0”). Of course, the display gear can be configured to be set either to “0” or the maximum number of doses that is expected of a particular type of metered dose inhaler assembly at the time that a new metered dose inhaler assembly is installed in the assistive device. The arrangement may thus be such that the numeral displayed in the aperture corresponds to a number of doses already delivered or corresponds to a number of projected doses remaining in the metered dose inhaler assembly.

Figure 3:
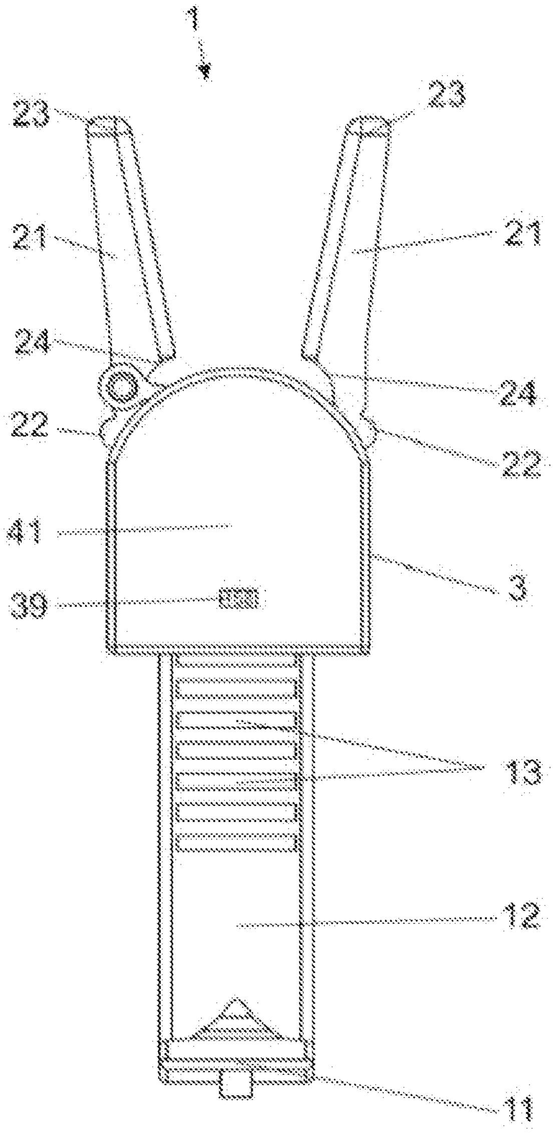
FIG. 3 is a front view of the assistive device of FIG. 1 with the metered dose inhaler removed.
Figure 4:
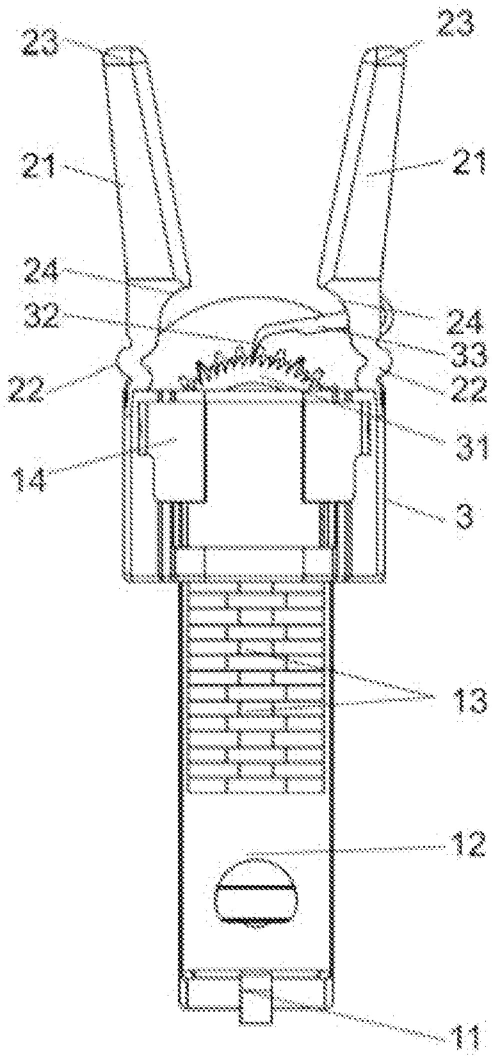
FIG. 4 is a rear view of the assistive device of FIG. 1 with the metered dose inhaler removed.

The visible front face of the body may be used to carry any type of indicia or ornamentation with a plain face being illustrated in FIG. 3 and a relief image cartoon character face (43) being illustrated in FIGS. 1, 2, 6 and 7. In the latter instance the levers can be made to appear as ears of the cartoon character and the leg may be provided with a simulated tail (44) (see FIG. 6) that can also be used as a handle for extending and retracting the leg as may be required.

In use, with a standard metered dose inhaler assembly installed within the assistive device, the levers can be moved towards each other to cause the cams to engage two opposite edges of the closed end of the canister to a move it in a direction towards the foot and mouthpiece supported by it until a dose of medication is delivered.

During this movement the transverse arm and pawl that it carries are moved inwards such that the pawl engages a tooth of the pawl driven gear to rotate it by an amount corresponding to the pitch of the gear teeth. When the arm and pawl return after the force is removed, the pawl moves over an adjacent tooth of the pawl driven gear and into a gap between the next two adjacent teeth ready for the next operation.

It will be understood that the transfer gear is only rotated by one gear tooth for every 10 doses administered by the metered dose inhaler assembly that in turn rotates the display gear by one tooth. A numeral reflecting either how many doses have been delivered by the metered dose inhaler or how many are remaining in the metered dose inhaler will be visible through the aperture (39).

The length of the leg and therefore the position of the foot can be easily adjusted by disengaging the locking member from the grooves in the leg and adjusting the position of the leg telescopically relative to the body of the assistive device. The assistive device can thus be used in combination with a number of different metered dose inhalers.

Referring to FIGS. 9 to 23, a second embodiment of an assistive device is illustrated. Similarly to the first embodiment, in the second embodiment, an assistive device (100) for a metered dose inhaler (102) comprises a body (103) defining a passage configured to receive a conventional metered dose inhaler assembly. The metered dose inhaler includes a canister (105) fitted with the usual outer sleeve having a transverse mouthpiece (107) with an axis of the canister (105) of the inhaler assembly approximately aligning with an axis of the passage through the body of the assistive device (100).

Figure 9:
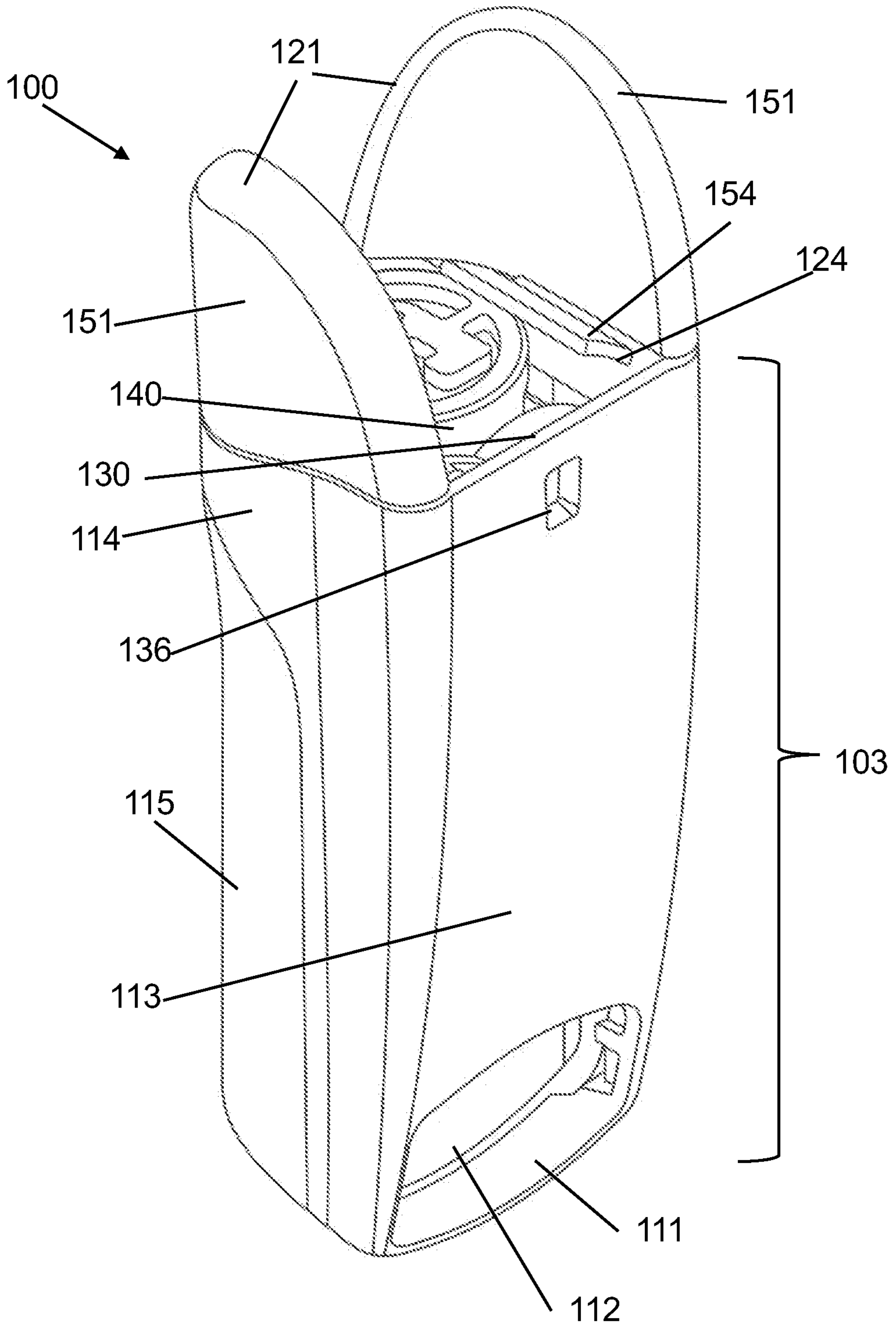
FIG. 9 is a perspective view of a second embodiment of an assistive device according to the invention.
Figure 10A:
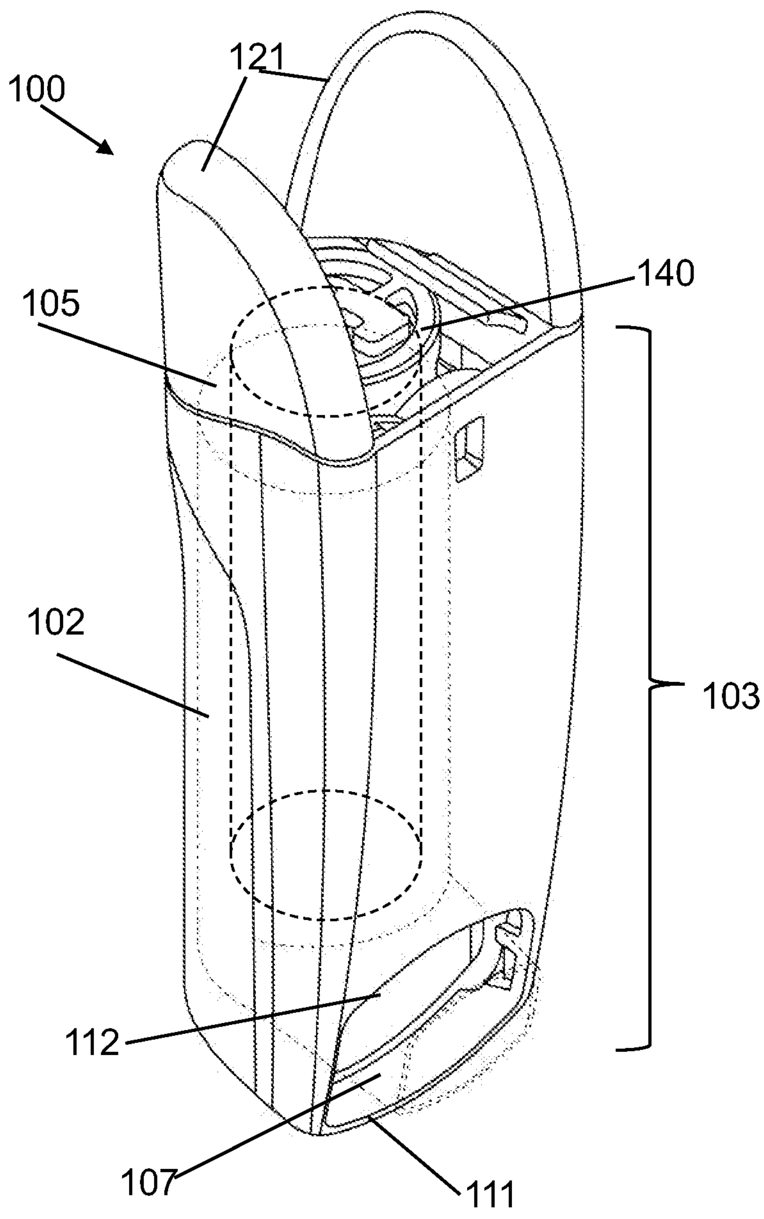
FIG. 10A is the perspective view of FIG. 9 showing a conventional metered dose inhaler (shown in broken lines) in position in the assistive device.
Figure 11:
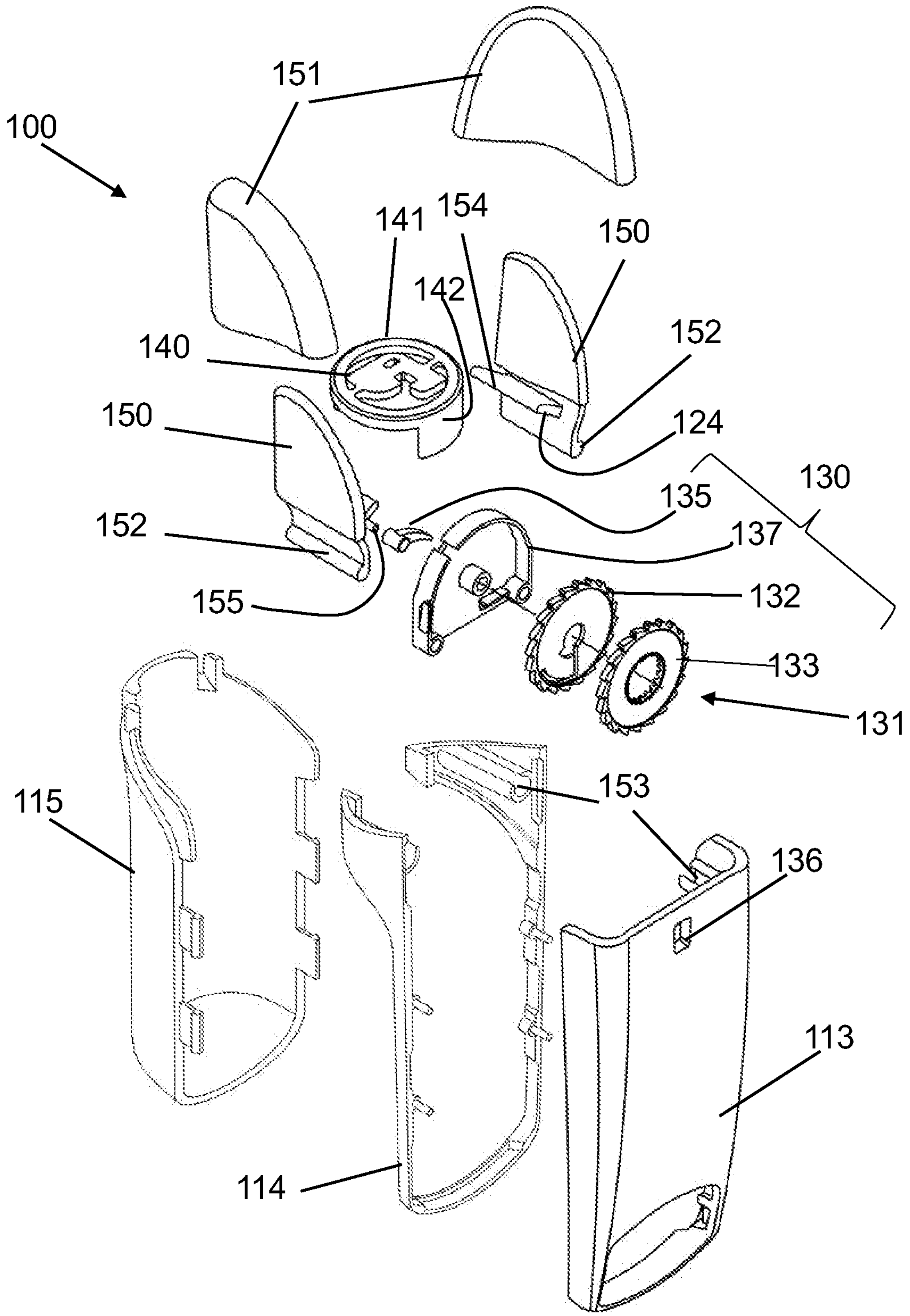
FIG. 11 is an exploded view of the second embodiment of the assistive device of FIG. 9.
Figure 12:
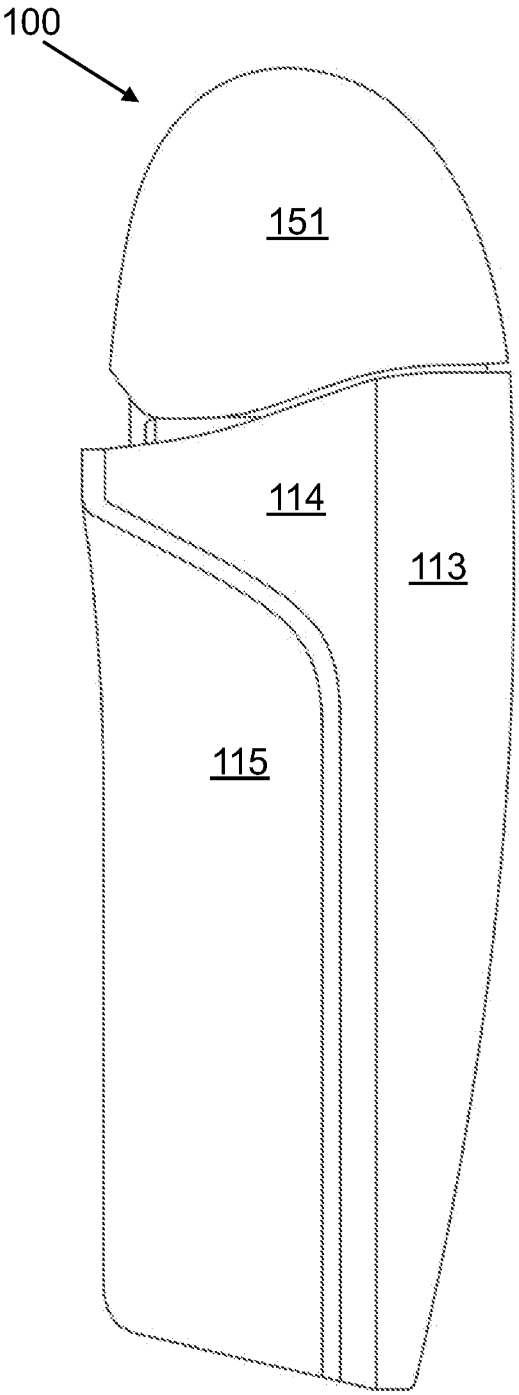
FIG. 12 is a side view of the second embodiment of the assistive device of FIG. 9.
Figure 13:
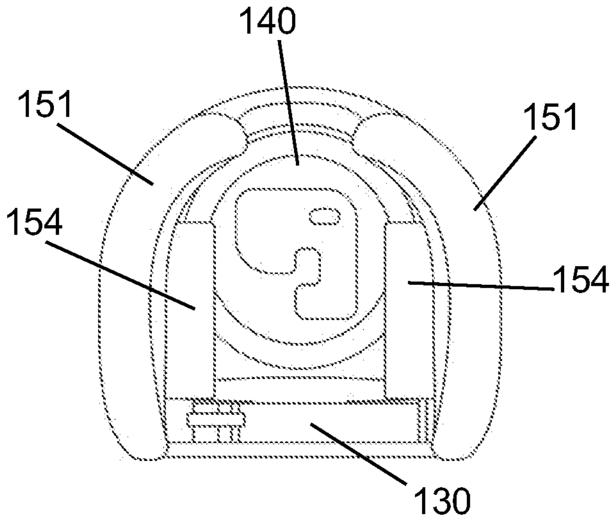
FIG. 13 is a top view of the second embodiment of the assistive device of FIG. 9.
Figure 14:
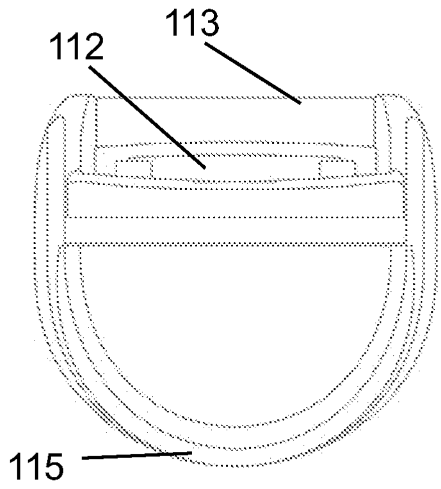
FIG. 14 is a bottom view of the second embodiment of the assistive device of FIG. 9.
Figure 15:
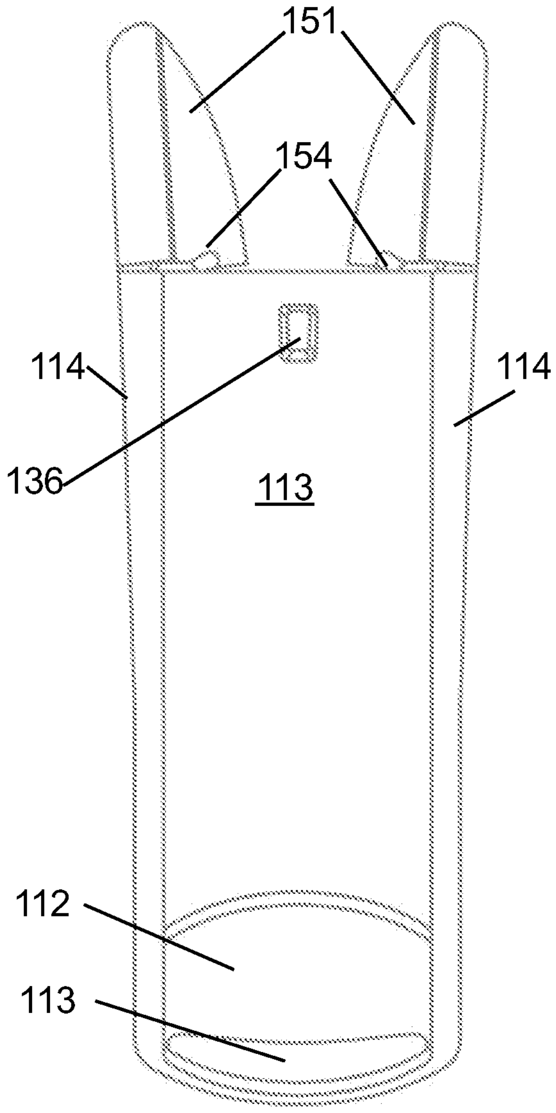
FIG. 15 is a front view of the second embodiment of the assistive device of FIG. 9.
Figure 16:
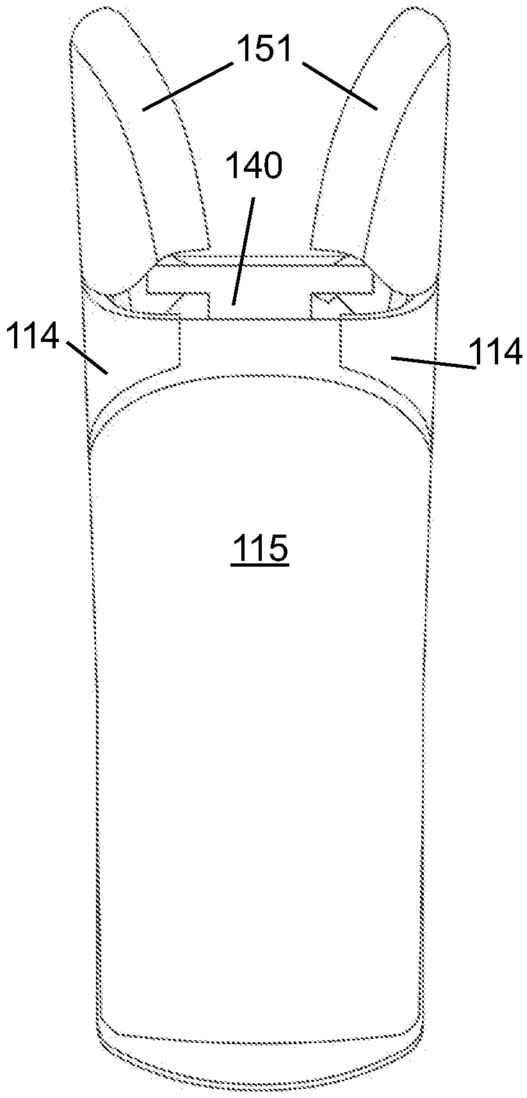
FIG. 16 is a back view of the second embodiment of the assistive device of FIG. 9.
Figure 17:
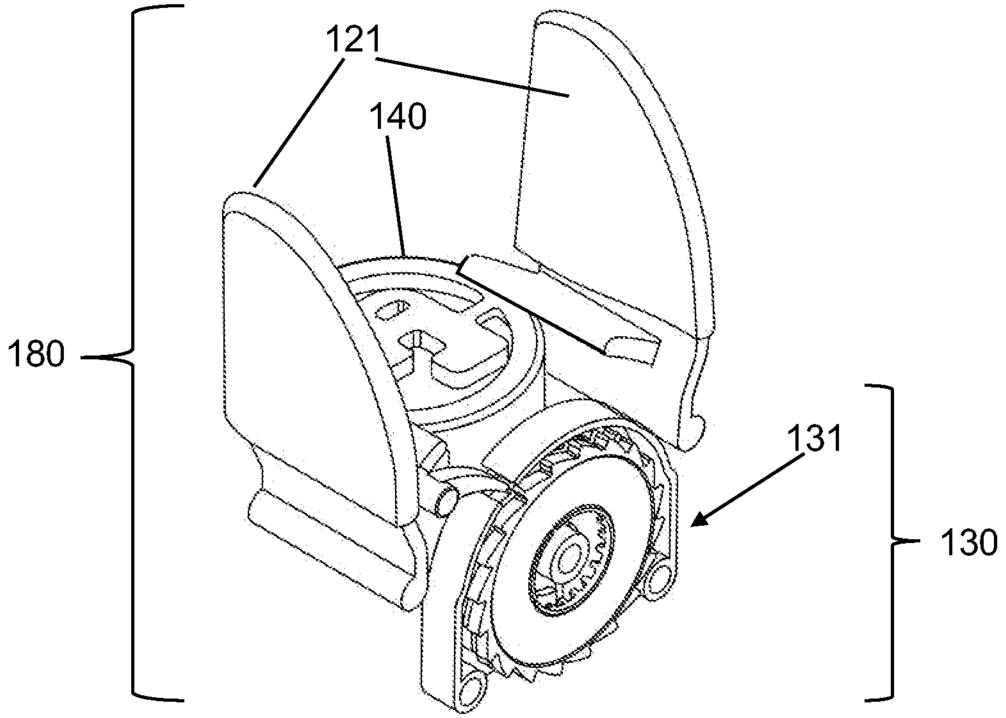
FIG. 17 is a perspective view of an upper portion of the second embodiment of the assistive device of FIG. 9 including the dose counter mechanism.
Figure 18:
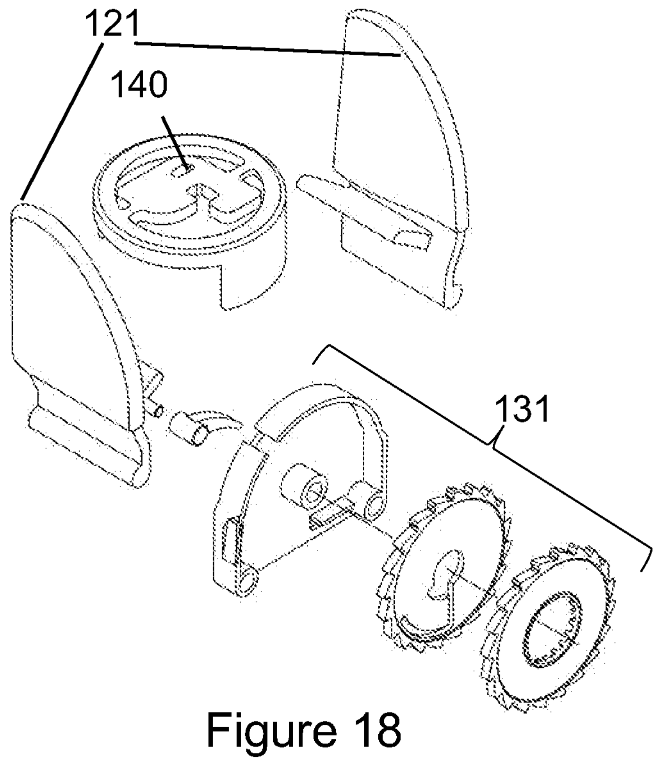
FIG. 18 is an exploded view of FIG. 17.

FIGS. 9 and 10A show a perspective view of the assistive device (100) of the second embodiment, with FIG. 10A showing a conventional inhaler (102) shown in broken lines. FIG. 11 shows an exploded view of the components. The body (103) defining the passage in the interior of the second embodiment is formed of injection moulded components. The body (103) is formed of a front housing (113) including a front outlet (112) that accommodates the transverse mouthpiece (107) of the inhaler (102), a middle housing (114), and a back housing (115). The front, middle, and back housings (113, 114, 115) together define the passage to accommodate the inhaler (102). The front housing (113) and the middle housing (114) include fastening elements to fasten them together. The front housing (113) extends around into side portions of the body (102). In an alternative arrangement, the front housing (113) and middle housing (114) may be formed of a single component. The back housing (115) includes a slide lock mechanism to removably attach it to the middle housing (114) to enable insertion and removal of the inhaler (102) into and from the body (102). The back housing (115) may be curved and extend around at least parts of the sides of the body (102).

In the second embodiment, two symmetrically arranged levers (121) are supported by the body (102) adjacent the passage and extend in a direction away from the top of the body (102) on either side of the body (102) at the top of the middle housing (114). In this embodiment, the levers (121) are each in the form of curved ears with an ear portion (150) that may be covered by an ear cover portion (151). The ear cover portion (151) is fastened to a top surface of the sides of the body (102) that are formed of the front and middle housings (113, 114) to form a smooth continuous outer surface of the body (102).

Figure 22:
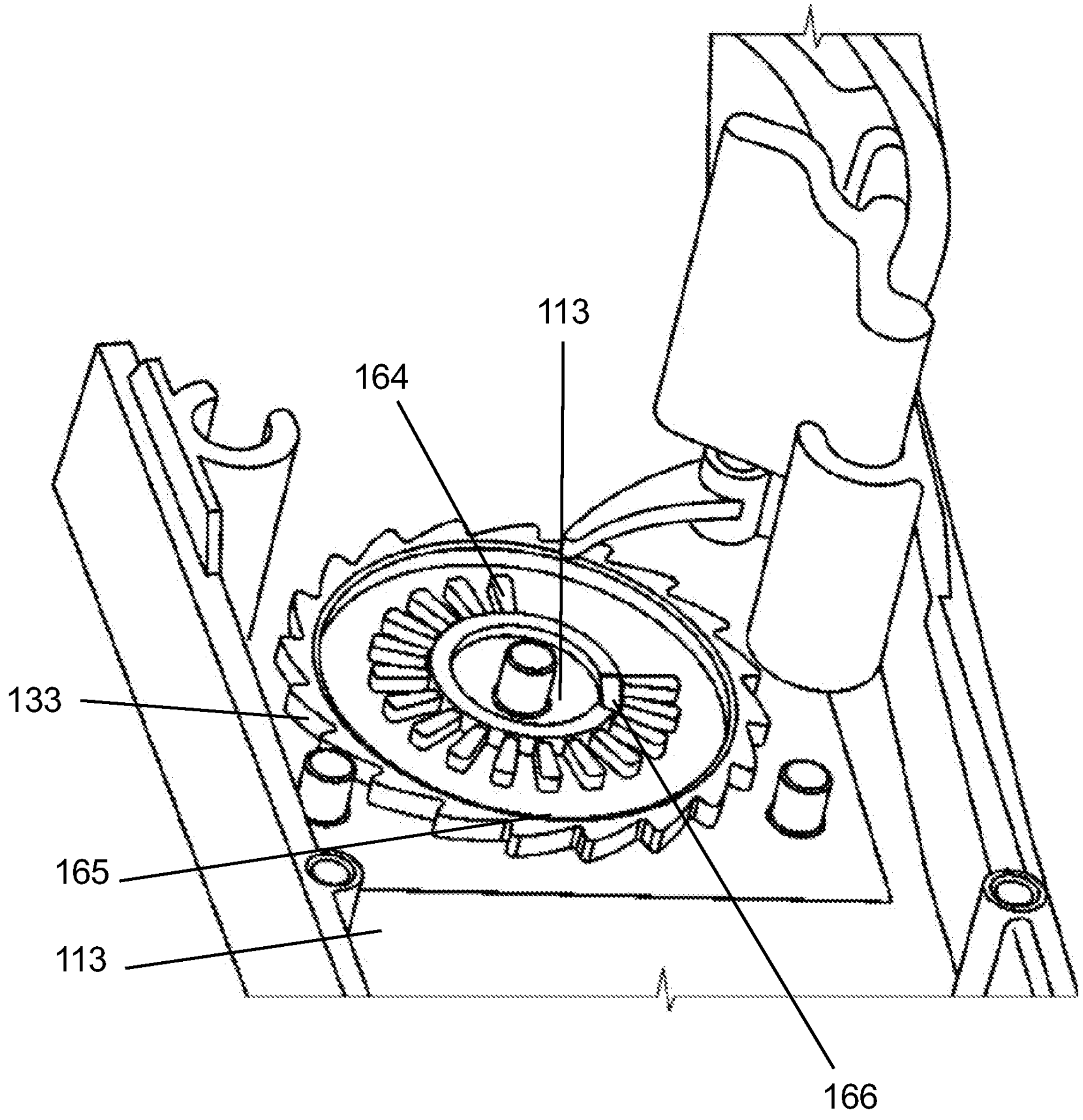
FIG. 22 is the perspective view of FIG. 21 with the ratchet gear removed to show the dial gear.
Figure 23:
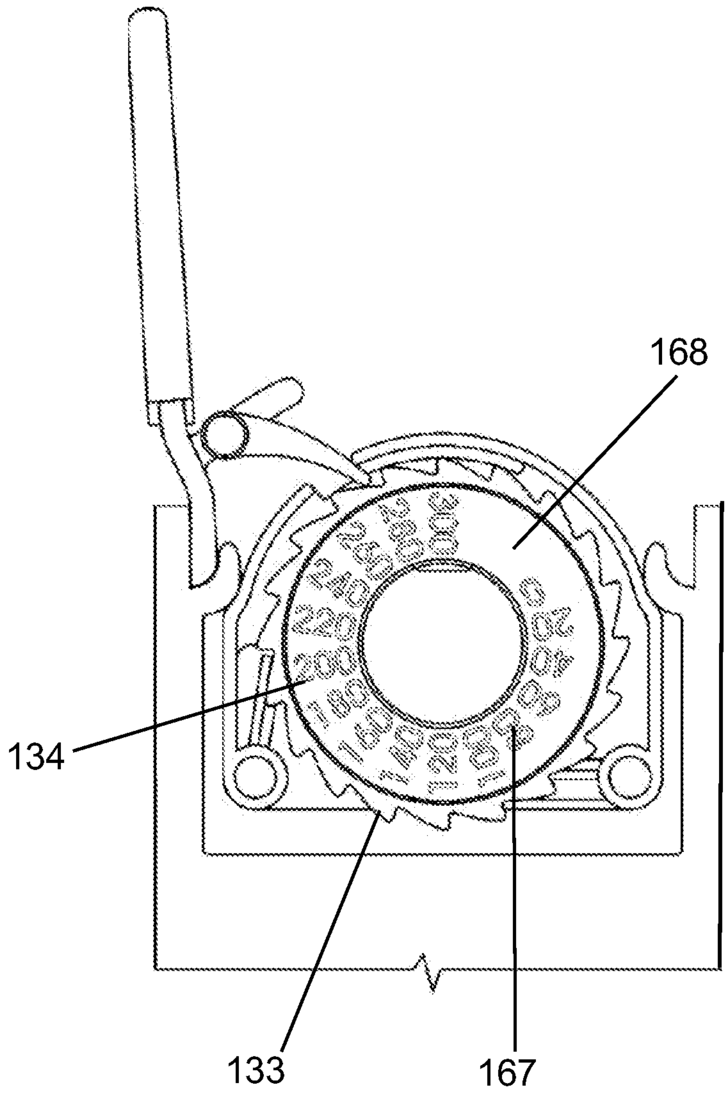
FIG. 23 is a perspective view of the upper portion of the second embodiment of the assistive device of FIG. 9 shown from the exterior of the assistive device with the front housing made transparent to show the dial gear.

Each ear portion (150) has a bottom extension that ends in an exterior-facing ridge (152) that forms a hinge joint in cooperation with a partially open cylindrical channel (153) that extends across a top portion of a side of the body (102), such as that formed of the front and middle housings (113, 114) as shown in FIG. 11. The hinge joint is also shown in FIGS. 22 and 23 below. This simple hinge joint and the natural spring-back of the gas filled inhaler canister (105) pushes the inner ear portion (150) back to a resting position. This has the benefit of no additional force resistance when activating the ears as the hinge joint is simply a hinge which has negligible frictional losses.

Each ear portion (150) includes a curved plate (154) extending transversely from the interior side of the ear portion (150) and forms a cam surface (124) to exert a force that is transferred to the operational end of the canister. The operation end is the end operated by a user to dispense. The force may be exerted on a closed end of the canister (105) either directly or via an intermediate component such as a height adjuster member (140). The curved plates (154) provide an efficient transmission of activation force to the canister (105). By arcing the contact point of the ear portion (150) to the height adjuster member (140) or the canister (105), a higher force component is transferred in the vertical axis. The curved plates (154) may be inwardly curved in a convex form or may be outwardly curved in a concave form. Alternatively, flat plates may be used. The curved plate (154) of one of the ear portions (150) includes a projection (155) for carrying a pawl member (135) that interacts with a dose counter mechanism (130) described below.

In the first embodiment, accommodation for different sizes of inhalers (102) is described using a rack and key mechanism which also served to fix the base of the inhaler relative to the levers. In the first embodiment, the inhalers engage the back of the sleeve which may need to accommodate height variations (up to ~7 mm) across different brands of inhalers.

In the second embodiment, the inhaler (102) is aligned so that the transverse mouthpiece (107) of the inhaler (102) sits on the front housing outlet (112) as shown in FIG. 10A. In this arrangement, the variation in heights of the inhalers is smaller (~2 mm) and the height variation across the inhalers may be solved with the use of a height adjuster member (140) that sits on top of the canister (105) for shorter inhalers.

Figure 10B:
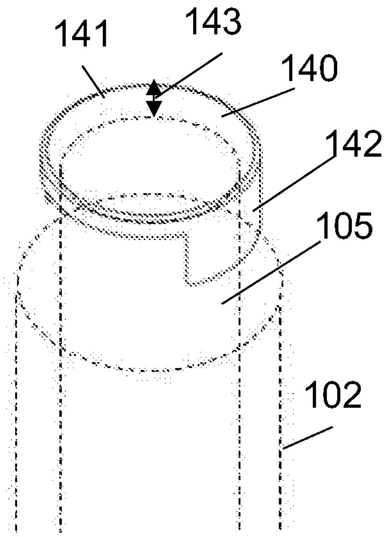
FIG. 10B is a detail of the perspective view of FIG. 10A showing a conventional metered dose inhaler (shown in broken lines) with a height adjuster member.

FIG. 10B shows the height adjuster member (140) in isolation for illustration. The height adjuster member (140) is a spacer member that adjusts the length of an inhaler (102) inserted into the assistive device (100), if required. The height adjuster member (140) fits on the top of a canister (105) of the inhaler (102) in the form of a cap (141) with side supports (142) and adds an extra height (143). The cap (141) has a depth that extends the height of the canister (105) and the side supports (142) hold the cap (141) in position on the canister (105). The height adjuster member (140) is optional and removable. It may be required for smaller dimensioned inhalers (102) whilst other inhalers (102) do not require it.

The height adjuster member (140) may have a decorative top or logo as it is viewed from the top of the assistive device (100).

FIGS. 12 to 16 show the assistive device (100) with the body (103) formed of the front, middle, and back housings (113, 114, 115) and ear cover portions (151) that provide a smooth and ergonomic device.

FIGS. 17 to 23 show a top portion (180) of the assistive device (100) including the dose counter mechanism (130) formed from cooperation of the levers (121) and the gear arrangement (131).

In the second embodiment, the dose counter mechanism (130) is provided in the form of a gear arrangement (131) activated by movement of one of the levers (121). The gear arrangement (131) is supported on the interior surface of the front housing (113) and the front housing (113) includes a dial display window (136) for displaying a dose counter.

The dose counter mechanism (130) is configured to be activated by at least a partial movement of the lever (121) to which the pawl member (135) is attached. The dose counter mechanism (130) activates first before the lever (121) is fully pushed down to activate the inhaler (102). This ensures that count doses are not overcounted. It is acceptable if the indication is that there are fewer doses than actually remaining as a safety mechanism.

The gear arrangement (131) of the dose counter mechanism (130) includes a first gear in the form of a racket gear (132) configured to be incremented by a pawl member (135) interfacing with the lever (121). The pawl member (135) may be supported by the projection (155) from the end of the curved plate (154) of one of the ear portions (150) providing the lever (121). A second gear in the form of a dial gear (133) is configured to rotate one increment when the ratchet gear (132) has completed a full revolution. The dial gear (133) provides a dial display (134) to display a number of delivered doses. As with the first embodiment, a ratchet and pawl are used to count activations in steps of X activations (for example, 20), then the dial moves one increment. A cover plate (137) encloses the gear arrangement (131) against the interior surface of the front housing (113).

Each activation rotates the ratchet gear (132) one increment and the pawl member (135) returns to the next tooth using a plastic spring member on the cover plate (137). The dial gear (133) in turn rotates one increment when the ratchet gear (132) has completed one revolution (20 increments) via a preloaded spring section in the ratchet gear (132). This spring section is held down on a ring on the front housing (113) which has a slot that lines up to when the dial gear (133) needs to rotate. When this happens the ratchet spring section latches to the dial gear (133) and allows it to move one increment.

Figure 19:
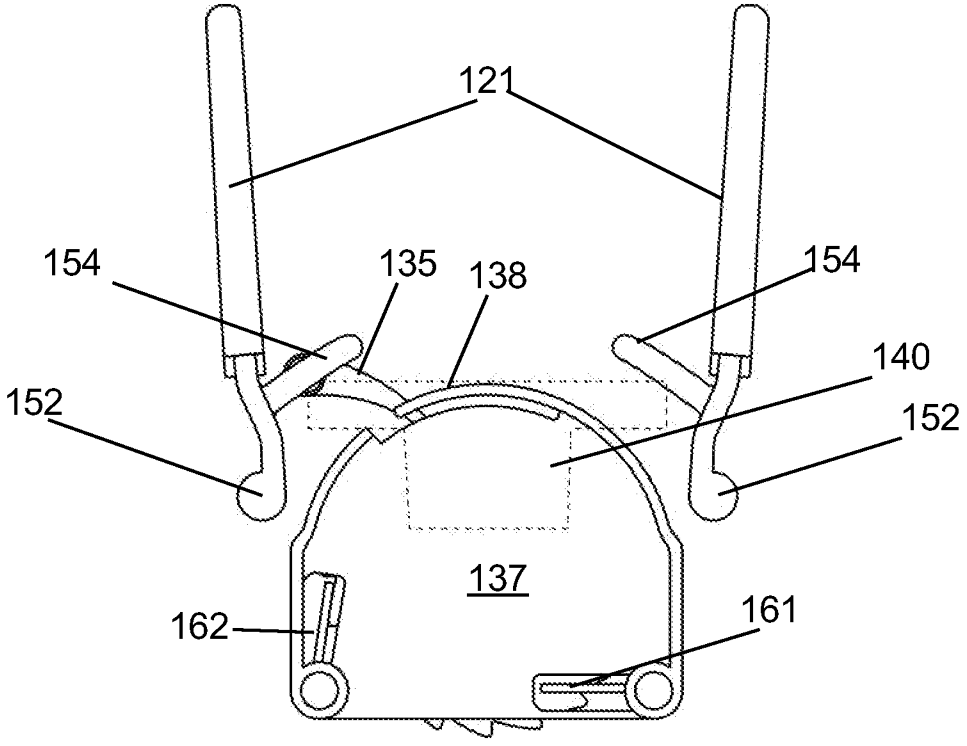
FIG. 19 is a side view of the dose counter mechanism of the second embodiment of the assistive device of FIG. 9 with the levers viewed from the interior of the assistive device.
Figure 20:
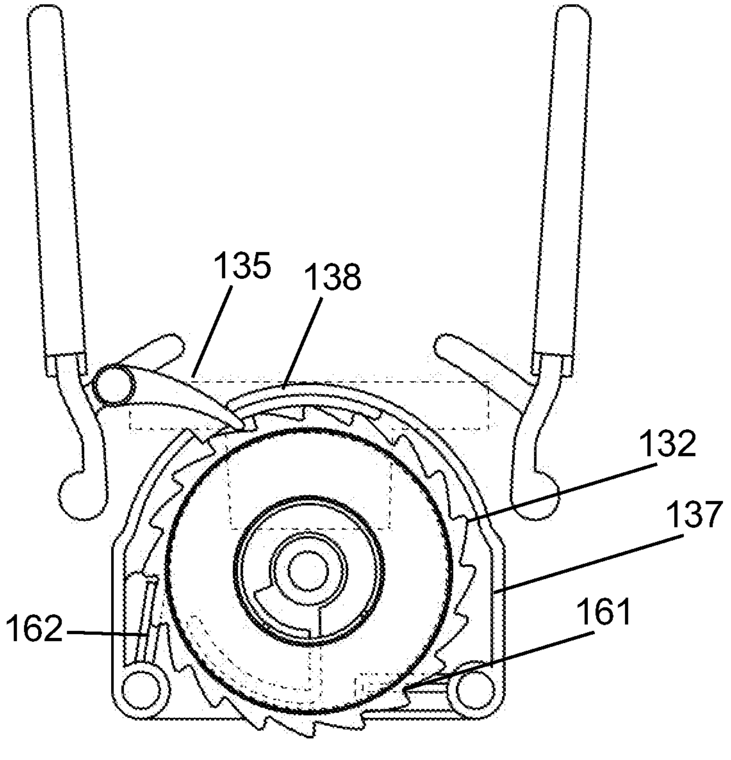
FIG. 20 is an opposite view of FIG. 19 from the exterior of the assistive device.

FIGS. 19 and 20 show the dose counter mechanism (130) looking from the interior of the assistive device (100) in FIG. 19 and looking from the exterior of the assistive device (100) (with the front housing not shown) in FIG. 20.

In FIGS. 19 and 20, the cover plate (137) is shown that rests on the interior side of the front housing (113). In addition to containing the components of the dose counter mechanism (130), the cover plate (137) fulfils three additional requirements:

1. A leaf spring component (138) depresses the pawl member (135) to always ensure contact between the pawl member (135) and the ratchet gear (132).
2. A first cover pawl (161) prevents the ratchet gear (132) from moving backwards (clockwise in the Figure) and provides an auditory "click" each time the device is activated.
3. A second cover pawl (162) prevents the dial gear (133) from moving backwards (clockwise in the Figure) and provides an auditory "click" after each full rotation of the first gear (132).

Figure 21A:
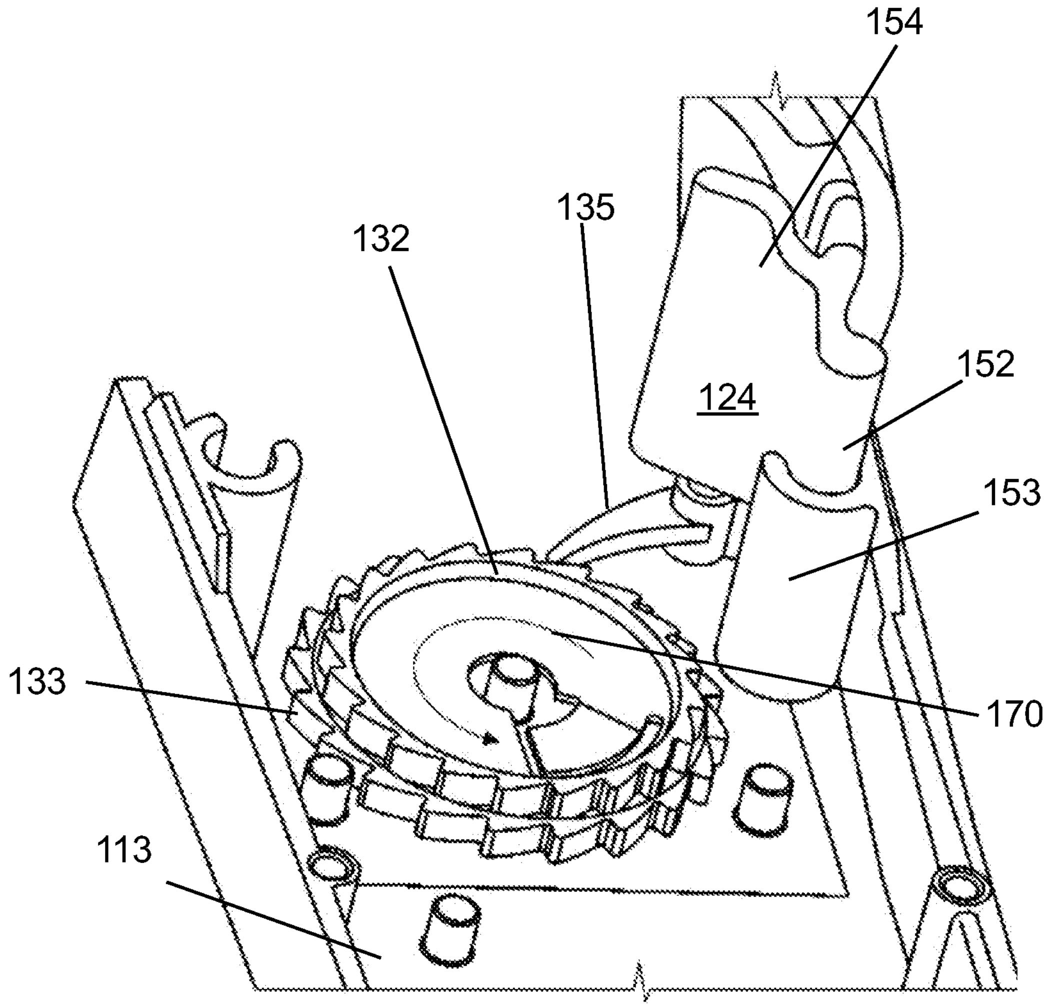
FIG. 21A is a perspective view of the upper portion of the second embodiment of the assistive device of FIG. 9 including a portion of the front housing and the ratchet and dial gears shown from the interior of the assistive device.

FIGS. 21A to 23 show the operation of the gear assembly (131) in more detail with the front housing (113) and the components of the lever (121) that operates the pawl member (135). FIGS. 21A and 22 show the gear assembly (131) from the interior of the assistive device (100). FIG. 23 shows the gear assembly (131) from the exterior of the assistive device (100) with the outer surface of the front housing (113) made transparent for illustration.

Figure 21B:
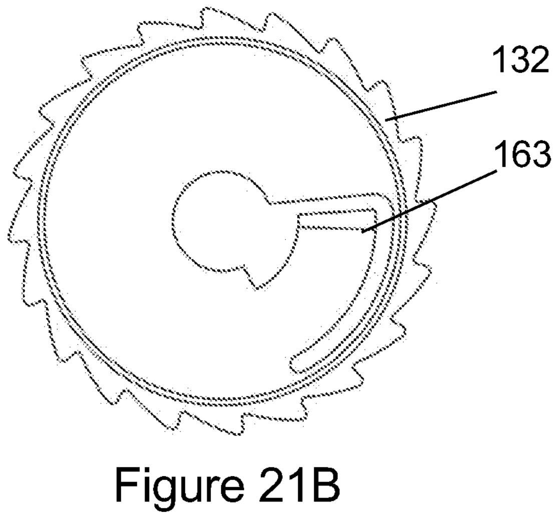
FIG. 21B shows the reverse side of the ratchet gear of FIG. 21.

Referring to FIG. 21A, behind the cover plate (137) lie the ratchet gear (132) and the dial gear (133). When the levers (121) are activated, the pawl member (135) moves forward as shown by the arrow (170). This rotates the ratchet gear (132) counter clockwise by one tooth/increment and is retained by the first cover pawl (161). For every activation of the levers (121), the ratchet gear (132) is advanced by one tooth and the ratchet gear (132) contains 20 teeth. After each full rotation of the ratchet gear (132) (i.e., on the 20th activation) the dial gear (133) is moved on by one gear/increment and retained by the second cover pawl (162). This may be referred to as "intermittent" operation. FIG. 21B shows the reverse side of the ratchet gear (132) including a dial tab (163) that projects out of the plane of the ratchet gear (132).

Referring to FIG. 22, during operation, the dial tab (163) on the reverse side of the ratchet gear (132) is elevated above the dial engagement teeth (164) as it slides along the sliding surface (166) of the front housing (113) and is not allowed to engage with the teeth (164) on the dial gear (133). However, after every 19th lever activation, the dial tab (163) aligns with a sliding recess (165) and the dial tab (163) descends into the recess (165) and locates between two dial engagement teeth (164). On the 20th activation, the dial gear (133) and the ratchet gear (132) turn together by one increment. After this single activation, the dial tab (163) slides out of the recess (165) onto the sliding surface (166) and disengages from the dial engagement teeth (164) to commence the next cycle. The ratchet gear (132) then rotates for 19 consecutive increments again whereafter the dial gear (133) is moved again on the 20th increment. This is then repeated until the canister (105) is empty.

Referring to FIG. 23, each increment of the dial gear (133) represents 20 activations and a dial display (134) of numbers (167) (for example, on a sticker) on the face (168) of the dial gear (133) indicates this through a viewing window (136) (shown in FIG. 11). With each rotation of the dial gear (133) (on the 20th activation of the device), the dial gear (133) moves with one increment and displays a number 20 lower than the previous number. The numbers (167) may start from a pre-set maximum number (for example, 300) through to 0. Once the canister (105) has been used to completion, a new inhaler (102) is placed within the body (103) of the assistive device (100) and the dial is manually rotated with a tool to reset to 300.

In trials conducted to date, the amount of force required to activate a standard inhaler without the assistive device of this invention was measured to be 39.23N. The amount of force required to activate the same inhaler with the assistive device of the invention was 12.26N which is a substantial improvement at relatively little additional cost when taking into account that the assistive device is reusable and does not have to be discarded with the inhaler. It should be noted that the force required to activate the inhaler described in US2003084899 would be greater than the 39.23N mentioned as that particular third order lever system would have a mechanical advantage of less than 1 whereas the mechanical advantage of the assistive device of the present invention is clearly greater than 1.

It should be understood that the assistive device of this invention can be used in combination with any simple standard inhaler and is not limited in its application to any one particular type provided that it has the adjustable leg and foot arrangement. In addition to that, the cross-sectional size of the passage through the body may be adjustable to accommodate different diameters of inhalers. This can most easily be achieved by forming a part of the body into a separate or integral strap that can be adjusted to adjust the cross-sectional size of the passage. Accordingly, a single assistive device according to the invention can be used many times in combination with many different standard inhalers.

It should be noted that the size of the body can be selected so that it can be comfortably held by a user and this may entail making it a little larger than the diameter of the inhaler in combination with which it is to be used.

It should also be noted that the invention is not limited to the provision of two levers and it is envisaged that, at least in the case of application to geriatrics, a three lever arrangement may be employed that lends itself to being gripped with a larger hand in order to move the levers towards each other in order to deliver a dose.

The assistive device of the invention also lends itself to use using additional fingers and that increases a patient's strength and thereby makes it easier to activate the inhaler with the assistive device attached. It does not "force" a child to use lateral force but rather gives the child the ability to do so. This means that the assistive device not only reduces the amount of force needed to deliver a dose, but allows for a patient to use additional fingers in which instance the assistive device is even more easily activated.

Whilst both of the two levers in the embodiment described above are movable about their proximal living hinge ends (22), it is envisaged that the principles of the invention would also be accomplished if one lever were fixed relative to the body and only the other one were movable thereby rendering the levers movable towards and away from each other as envisaged above. It may be that this variation of the invention would not be quite as effective as that described above. The relatively fixed lever would function as a lever although it does not have a specific fulcrum of its own.

In so far as the lever arrangement is concerned, it will be understood that the principles of this invention can be applied to an inhaler that is not of the metered dose type whilst the dose counter would most appropriately be applied only to metered dose types of inhalers.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. An assistive device for an inhaler, wherein the assistive device comprises:

a body defining a passage configured to receive a conventional inhaler assembly, the conventional inhaler assembly including a canister and transverse mouthpiece with an axis of the canister of the inhaler assembly approximately aligning with an axis of the passage through the body of the assistive device, a base support associated with the body for supporting the mouthpiece of the inhaler assembly at one end of the body when the inhaler assembly is installed therein, and at least two symmetrically arranged levers supported by the body adjacent the passage and extending in a direction away from the base support and generally parallel to an axis of the body with a proximal end of each of the levers being attached to the body by an attachment that enables a free opposite end of at least one of the levers to be moved towards and away from the other of the levers, wherein the attachment is a hinge joint configured to return the lever to a starting position in cooperation with a return of the canister to a rest position after dispensing the medicament, and an inwardly directed cam surface of at least one of the levers that is configured to exert a force on a closed end of the canister of the inhaler assembly when it is installed in the assistive device to move the canister longitudinally towards the base support and cause medicament to be dispensed from the canister.

2. The assistive device as claimed in claim 1, including a height adjuster member disposed between the inwardly directed cam surface and the closed end of the canister.

3. The assistive device as claimed in claim 2, wherein the height adjuster member is configured to attach to the closed end of the canister to adjust the height of the canister.

4. The assistive device as claimed in claim 3 in which there are two levers symmetrically arranged relative to the passage with the cam surfaces thereof projecting into the passage so as to cooperate with corners of a closed end of the canister or corners of the height adjuster member.

5. The assistive device as claimed in claim 1, wherein the cam surface of at least one of the levers is curved inwardly and configured to achieve a suitable longitudinal movement of the canister during movement of the levers towards each other so that medication is delivered by appropriate operation of the levers.

6. The assistive device as claimed in claim 1, the attachment enables the free opposite ends of two opposing levers to be moved towards each other to move the inwardly directed cam surface of the at least one of the levers.

7. The assistive device as claimed in claim 1, wherein the base support includes a front outlet configured to support the transverse mouthpiece of the inhaler assembly.

8. The assistive device as claimed in claim 1, including a dose counter mechanism in the form of a gear arrangement activated by movement of one of the levers.

9. The assistive device as claimed in claim 8, wherein the gear arrangement is configured to be activated by at least a partial movement of the lever.

10. The assistive device as claimed in claim 8, wherein the gear arrangement includes a first gear configured to be incremented by a pawl interfacing with the lever and a second gear configured to rotate one increment when the first gear has completed a full revolution, wherein the second gear provides a dial display to display a number of delivered doses.

11. The assistive device as claimed in claim 1, wherein the at least two symmetrically arranged levers are in an arrangement complying with a second order lever system in which the mechanical advantage is greater than 1.

12. The assistive device as claimed in claim 11, wherein lengths of the levers are selected according to the mechanical advantage to be achieved.

13. The assistive device as claimed in claim 1, wherein the at least two symmetrically arranged levers are attached to an end of the body opposite to the end of the body having the base support and extend in a direction away from the body.

14. An assistive device for an inhaler, wherein the assistive device comprises:

a body configured to removably receive the inhaler substantially within the body, the body including a base support configured to engage with a mouthpiece end of the inhaler;

two opposed levers extending longitudinally from the body at an opposite end of the body to the base support, wherein at least one of the levers has a hinge attachment to the body for operation by squeezing the levers together and the at least one of the levers has an inwardly directed cam surface at the hinge attachment configured to exert a force on an operational end of the inhaler as the levers are squeezed together, wherein the hinge attachment is a hinge joint configured to return the lever to a starting position in cooperation with a return of the inhaler to a rest position after dispensing the medicament.

15. The assistive device as claimed in claim 14, wherein the two opposed levers both have the hinge attachment to the body and the inwardly directed cam surface, with the cam surface of the at least one levers exerting a force in a direction towards the base support of the body.

16. The assistive device as claimed in claim 14, wherein the inwardly directed cam surface exerts the force on the operational end of the inhaler via a height adjustment member.

17. The assistive device as claimed in claim 14, wherein the inwardly directed cam surface is a convex curved surface.

18. The assistive device as claimed in claim 14, wherein the base support is configured to engage with a mouthpiece of the inhaler.

19. The assistive device as claimed in claim 14, including a dose counter mechanism in the form of a gear arrangement activated by movement of one of the levers, wherein the gear arrangement is configured to be activated by at least a partial movement of the lever.

* * * * *